United States Patent

Kaneko et al.

[11] Patent Number: 5,518,665
[45] Date of Patent: May 21, 1996

[54] TRANSPARENT SOLID DETERGENTS

[75] Inventors: Daisuke Kaneko; Kazutami Sakamoto, both of Kawasaki, Japan

[73] Assignee: Ajinomoto Co., Inc., Tokyo, Japan

[21] Appl. No.: 295,674

[22] PCT Filed: Jan. 10, 1994

[86] PCT No.: PCT/JP94/00018

§ 371 Date: Oct. 24, 1994

§ 102(e) Date: Oct. 24, 1994

[87] PCT Pub. No.: WO94/16041

PCT Pub. Date: Jul. 21, 1994

[30] Foreign Application Priority Data

Jan. 11, 1993 [JP] Japan ................... 5-002609

[51] Int. Cl.$^6$ ...................................... C11D 1/04
[52] U.S. Cl. .................. 252/546; 252/541; 252/544; 252/174; 252/DIG. 16; 252/DIG. 5
[58] Field of Search ................ 252/546, 541, 252/544, 174, DIG. 16, DIG. 5

[56] References Cited

U.S. PATENT DOCUMENTS

| | | | |
|---|---|---|---|
| 3,663,459 | 5/1972 | Yoshida et al. | 252/546 |
| 3,926,828 | 12/1975 | O'Neill et al. | 252/117 |
| 4,165,293 | 8/1979 | Gordon | 252/118 |
| 4,273,684 | 6/1981 | Nagashima et al. | 252/544 |
| 5,098,608 | 3/1992 | Miyazawa et al. | 252/546 |

FOREIGN PATENT DOCUMENTS

| | | |
|---|---|---|
| 10921 | 4/1973 | Japan . |
| 107012 | 9/1977 | Japan . |
| 46841 | 12/1978 | Japan . |
| 18716 | 5/1985 | Japan . |
| 1129 | 1/1992 | Japan . |

OTHER PUBLICATIONS

Database WPI, Derwent Publications Ltd., AN 81–58023D [32], "Preparation of Transparent Pasty Detergent", JP–A–56 076 500, Jun. 24, 1981.

Primary Examiner—Paul Lieberman
Assistant Examiner—Michael P. Tierney
Attorney, Agent, or Firm—Oblon, Spivak, McClelland, Maier & Neustadt

[57] ABSTRACT

A transparent solid detergent comprising N-acylglutamic acid salts, characterized in that said salts are the potassium and sodium salts, each having a neutralization degree of between 1.5 and 2.0, said potassium and sodium salts being in a molar ratio of 9:1 to 2:8 and being incorporated in a combined amount of 30 to 70% of the total weight of said detergent. The detergents of the present ingention moisturize with less irritation to skin, etc. They have good storage stability and usabilities and are especially suitable as facial soap.

4 Claims, No Drawings

TRANSPARENT SOLID DETERGENTS

TECHNICAL FIELD

This invention relates to N-acylglutamic acid salt-containing solid detergent compositions with mild action on skin and hair, and more specifically to N-acylglutamic acid salt-containing transparent solid detergents with improved storage stability while maintaining usabilities such as sudsing, detergency, etc.

BACKGROUND ART

Transparent soap (transparent solid detergents) is commercially valuable because of the high-grade impression by its transparency. Most of prior transparent solid detergents are made from higher fatty acid soap as the base and transparentizers such as glycerin, sucrose, sorbitol, etc. They are made by framing or milling, and in general, framed transparent soap has better transparency than milled soap. However, framing is not suitable for mass production because it takes about one month to obtain a stabilized shape. Moreover, it is known that higher fatty acid soap-based transparent soap made by these processes is not essentially different from ordinary opaque soap, that the former has the same drawbacks as the latter, e.g., irritation to skin, poor sudsing in hard water, and that it may opacify in use.

JPA55-25465 (i.e., Japanese patent application laid-open (tokkai) No. Sho 55-25465), discloses transparent solid detergents based on N-longchain acyl acidic amino acid salts, and JPA56-76499 discloses a method of manufacturing milled transparent solid detergents using N-long chain acylglutamic acid salts.

However, such transparent solid detergents disclosed in these patent documents have low storage stability, because the triethanolamine salt or the sodium salt is used as the N-longchain acylglutamic acid salt. Thus, the triethanolamine salt-based detergents become browned when stored at high temperatures, and the sodium salt-based detergents gradually crystalize during storage and finally opacify. Moreover, these transparent solid detergents still need further improvement on their usabilities such as sudsing, disintegration, adhesion, etc.

In view of the prior art described above, an object of this invention is to provide N-longchain acylglutamic acid salt-containing transparent solid detergents which have improved usabilities such as sudsing, disintegration, adhesion, etc., while maintaining storage stability in connection with their transparency and non-coloration, and which are less irritant to skin, hair, ocular mucosa, etc.

DISCLOSURE OF THE INVENTION

As the results of elaborate studies to attain the above object, the present inventors have found that less irritant transparent solid detergents which are free from coloration and crystallization and are provided with good storage stability enough to maintain their transparency and with good usabilities such as sudsing, disintegration, adhesion, etc. can be obtained by using concurrently as the base two certain salts of N-acylglutamic acid, namely the potassium and sodium salts each having a certain neutralization degree in a certain ratio, and thus completed this invention on the basis of those findings.

Therefore, this invention relates to a transparent solid detergent comprising N-acylglutamic acid salts characterized in that said salts are the potassium and sodium salts, each having a neutralization degree of between 1.5 and 2.0, said potassium and sodium salts being in a molar ratio of 9:1 to 2:8 and being incorporated in a combined amount of 30 to 70% by weight of the total weight of said detergent.

This invention will now be explained in detail, as follows.

The acyl groups of the N-acylglutamic acid salts used in the transparent solid detergents according to this invention are those which can be derived from saturated or unsaturated fatty acids having 10 to 22 carbon atoms, e.g., those derivable from single composition fatty acids such as lauric acid, palmitic acid, stearic acid, and oleic acid. The acyl groups can also be those derivable from mixed fatty acids from the natural source such as coconut oil fatty acid, tallow fatty acid, hardened tallow fatty acid, etc., as well as those derivable from chemically synthesized fatty acids (including branched fatty acids).

According to this invention, the N-acylglutamic acid salts are the potassium and sodium salts, each having a neutralization degree of between 1.5 and 2.0, preferably between ]1.7 and 1.9, and they are concurrently used in a molar ratio of 9:1 to 2:8, preferably 8:2 to 3:7.

The "neutralization degree" as used herein is defined as the molar ratio of the alkaline metal moiety to the N-acylglutamate radical moiety in the composition of the salt concerned. For example, the neutralization degree of the N-acylglutamic acid sodium salt obtained by neutralizing 1 mol of N-acylglutamic acid with 1.7 mol of sodium hydroxide is 1.7. It is not preferable to choose a neutralization degree outside the above range for any of the potassium and sodium salts. Below the lower limit, the transparency deteriorates, while above the upper limit, the high-temperature stability deteriorates.

If the ratio of the potassium salt to the sodium salt is above the specified upper limit, the resulting transparent solid detergents are liable to disingetrate in water, while below the specified lower limit, the resulting detergents get crystallized in time and thus opacity. Other salts may also be used in combination with the potassium and sodium salts, but this may result in lower storage stability of the resultant transparent solid detergents. Accordingly, it is preferable according to this invention, to limitatively use a combination of the potassium and sodium salts.

The N-acylglutamic acid salts should be incorporated in a transparent solid detergent according to this invention, though depending on the ratio of the potassium salt to the sodium salt, in an amount of 30 to 70%, preferably 40 to 65% of the total weight of the transparent solid detergent. Too small an amount can not produce the intended effect, while an extremely large amount results in opacity.

The transparent solid detergents according to this invention have no special limitations on their starting materials, and any starting materials commonly found in known transparent soap may be used, so far as the two N-acylglutamic acid salts described above are concurrently used in the specified combined amount. Namely, starting materials other than the N-acylglutamic acid salts incorporated in an amount of within such range may include known transparentizers and other additives.

For example, the transparency can be enhanced by adding transparentizers commonly used in known transparent soap, e.g., polyvalent alcohols such as glycerin, diglycerin, ethylene glycol, propylene glycol, butylene glycol, and sorbitol; sugars such as dextrose, fructose, and sucrose; thiourea; urea; and maltol.

In addition to such transparentizers, the transparent solid detergents according to this invention may naturally comprise other approprioate additives such as oil, perfume, colorant, and preservative, if necessary or desired. Further, naturally they may also comprise other anionic surface active agents, amphoteric surface active agents, nonionic surface active agents, cationic surface active agents, humectants, fungicides, chelating agents, antioxidants, herb medicine, and water-soluble polymers, in order to regulate their detergency, sudsing, etc., insofar as the transparency is not affected.

There are no special limitations on the process for producing the transparent solid detergents according to this invention, and they may be manufactured either by any conventional framing method or milling method. Thus, framed soap is prepared by mixing a lower alcohol such as ethanol, N-acylglutamic acid salts and q.s. water, optionally with transparentizers and other additives, dissolving the mixture thoroughly, aging it for about 1 month, and then stamping. This method has lower productivity than the milling one, but the transparency of the resultant transparent solid detergents is generally better. Milled soap is prepared by, for example, mixing all the starting materials thoroughly with a roll or pelletizer, feeding the mixture to a plodder used in the conventional soapmaking process, and then stamping.

THE BEST MODE FOR CARRYING OUT THE INVENTION

The following examples will illustrate this invention.

In the examples, all the test samples of solid detergents were prepared by milling. The evaluation of the test samples of solid detergents was made by the procedures described below. All the percentages indicated in the examples are by weight.

(a) Transparency:

A sample cut in a thickness of 1 cm was placed on printed characters of 12 points to examine if they can be identified through the sample.

The evaluation is as follows: ○, clearly identified; △, barely identified; and ×, unidentified.

(b) Sudsing:

The measurement of sudsing was based on Ross-Miles Test (JIS K 3362). Sudsing was evaluated from the height (ml) of the suds after 5 minutes at a temperature of 40° C. and the sample concentration of 0.50%.

The evaluation is as follows: ○, more than 240 ml; △, 200 to 240 ml; and ×, less than 200 ml.

(c) Room temperature stability:

Each test sample was observed after it had been allowed to stand at 25° C. for 1 month.

The evaluation is as follows: ○, no change in transparency after 1 month; △, slight loss of transparency; and ×, opacified by crystallization.

(d) High temperature stability:

Each test sample was observed for the change in hue and odor after it had been allowed to stand at 50° C. for 3 weeks.

The evaluation is as follows: ○, no change in transparency after 3 weeks; △, slight change in hue; and ×, significant change in hue.

(e) Hardness:

Each test sample was tested by hand touch to determine whether it was sufficiently hard for use as solid detergent.

The evaluation is as follows: ○, sufficiently hard; △, not sufficiently hard; and ×, too soft for practical use.

(f) Disintegration:

Each sample was immersed in water for 1 hour, being suspended with a kite string, to determine the decrease in mass (%).

The evaluation is as follows: ○, less than 10% decrease in mass; △, 10 to 20%; and ×, more than 20%.

(g) Adhesion:

After 30 g of each sample was allowed to stand for 24 hours in a plastic soap case containing 1 ml of purified water, it was determined whether the sample adhered to the case could be easily removed therefrom.

The evaluation is as follows: ○, easily removed; △, not easily removed; and ×, very difficult to remove.

COMPARATIVE EXAMPLES 1 to 3

A sample of transparent solid detergent was prepared from each of the salts (neutralization degree, 1.8) of N-cocoylglutamic acid shown in the following Table 1 and evaluated. Each sample was composed of 50% of the N-cocoylglutamic acid salt and 50% of purified water. The evaluation results are also shown in Table 1.

TABLE 1

| Comparative Examples | 1 | 2 | 3 |
|---|---|---|---|
| Salt | Triethanolamine salt | Sodium salt | Potassium salt |
| Transparency | △ | ○ | ○ |
| Sudsing | △ | ○ | ○ |
| RT stability | ○ | × | ○ |
| HT stability | × | × | ○ |
| Hardness | △ | ○ | ○ |
| Disintegration | × | ○ | × |
| Adhesion | △ | ○ | △ |

It is evident from Table 1 that the triethanolamine salt-based sample had low stability at high temperature, and thus became browned and deteriorated in transparency. The sodium salt-based sample showed good transparency, but it had low stability both at high temperature and room temperature so that it gradually crystallized and opacified. The potassium salt-based sample was good both in transparency and stability, but was inferior in quality to the sodium salt sample in connection with disintegration.

EXAMPLES 1 to 3 and COMPARATIVE EXAMPLES 4 to 7

Each combination of the salts of N-cocoylglutamic acid shown in the following Table 2 (neutralization degree, 1.8) was used to prepare a sample of transparent solid detergent and tested by the procedures described above. Each sample was composed of 50% of the N-cocoylglutamic acid salts and 50% of purified water. The test results are also shown in Table 2.

TABLE 2

| Examples | | | | 1 | 2 | 3 | |
| Comparative Examples | 4 | 5 | 6 | | | | 7 |
|---|---|---|---|---|---|---|---|
| Sodium salt | — | 50 | 5 | 10 | 50 | 80 | 90 |
| Potassium salt | 50 | — | 95 | 90 | 50 | 20 | 10 |
| Triethanolamine salt | 50 | 50 | — | — | — | — | — |
| Transparency | △ | △ | ○ | ○ | ○ | ○ | ○ |
| Sudsing | ○ | ○ | ○ | ○ | ○ | ○ | ○ |
| RT stability | ○ | ○ | ○ | ○ | ○ | ○ | △ |
| HT stability | × | × | ○ | ○ | ○ | ○ | × |
| Hardness | △ | ○ | ○ | ○ | ○ | ○ | ○ |
| Disintegration | △ | △ | △ | ○ | ○ | ○ | ○ |

TABLE 2-continued

| Examples<br>Comparative Examples | 4 | 5 | 6 | 1 | 2 | 3 | 7 |
|---|---|---|---|---|---|---|---|
| Adhesion | Δ | Δ | Δ | O | O | O | O |

It is evident from Table 2 that the test samples prepared by using a combination of the sodium and triethanolamine salts or the potassium and triethanolamine salts were less stable at high temperatures and became colored, in contrast to the test samples prepared by using a combination of the potassium and sodium salts. When the proportion of the potassium salt exceeded 90%, the sample deteriorated in quality in connection with disintegration. When it was below 20%, the stability both at room temperature and high temperatures deteriorated.

EXAMPLES 4 to 8, COMPARATIVE EXAMPLES 8 to 11

Test samples of transparent solid detergents were prepared using combinations of the potasium salt and the sodium salt of N-cocoylglutamic acid in a fixed molar ratio of 6:4, with varied neutralization degrees and combined amounts of the N-cocoylglutamic acid salts as shown in the following Table 3, and evaluated. The evaluation results are also shown in Table 3.

TABLE 3

| Examples<br>Comparative Examples | 8 | 4 | 5 | 6 | 9 | 10 | 7 | 8 | 11 |
|---|---|---|---|---|---|---|---|---|---|
| Neutralization degree | 1.4 | 1.5 | 1.8 | 2.0 | 2.1 | 1.8 | 1.8 | 1.8 | 1.8 |
| Total amount | 50 | 50 | 50 | 50 | 50 | 25 | 30 | 70 | 75 |
| Transparency | Δ | Δ | O | O | O | liq-uid | O | O | Δ |
| Sudsing | O | O | O | O | Δ | — | O | O | O |
| RT stability | X | O | O | O | O | — | O | O | Δ |
| HT stability | Δ | O | O | Δ | X | — | O | O | X |
| Hardness | Δ | O | O | O | O | — | Δ | O | Δ |
| Disintegration | Δ | O | O | O | O | — | O | O | Δ |
| Adhesion | Δ | O | O | O | O | — | O | O | Δ |

It is evident from Table 3 that the samples having a neutralization degree of 1.5 or less deteriorated in transparency, and that the sample having a neutralization degrees of 2.0 or more deteriorated in high temperature stability and became browned. When the combined amount of the N-cocoylglutamic acid salts was below 30%, the sample was liquid. When it was above 70%, the transparency deteriorated. Accordingly, the combined or total amount of the N-cocoylglutamic acid salts is preferably 30 to 70%.

EXAMPLES 9 to 12

(a) A sample of transparent solid detergent of the composition shown in the following Table 4 was prepared and evaluated by the procedures described above. The results were satisfactory in all test items (Example 9).

TABLE 4

| Ingredients | Content (%) |
|---|---|
| N-cocoylglutamic acid salt<br>(Neutralization degree, 1.8;<br>Potassium salt:sodium salt = 6:4) | 45 |
| D-Sorbitol | 30 |
| Glycerin | 5 |

TABLE 4-continued

| Ingredients | Content (%) |
|---|---|
| Polyethylene glycol (MW, 20,000) | 3 |
| Sodium pyroglutamate | 3 |
| Diethanolamide laurate | 3 |
| Cationized cellulose | 2 |
| Sorbitan monostearate | 1 |
| Purified water | balance |

(b) A sample of transparent solid detergent of the composition shown in the following Table 5 was prepared and evaluated by the procedures described above. The results were satisfactory in all test items (Example 10).

TABLE 5

| Ingredients | Content (%) |
|---|---|
| N-Cocoylglutamic acid salt<br>(Neutralization degree, 1.6;<br>Potassium salt:sodium salt = 8:2) | 60 |
| Sugar | 10 |
| Polyethylene glycol | 5 |
| Glycerin | 5 |
| Sodium lactate | 3 |
| Hydroxypropyl cellulose | 1 |
| Preservative | q.s. |
| Purified water | balance |

(C) A sample of transparent solid detergent of the composition shown in the following Table 6 was prepared and evaluated by the procedures described above. The results were satisfactory in all test items (Example 11).

TABLE 6

| Ingredients | Content (%) |
|---|---|
| N-Lauroylglutamic acid | 25 |
| N-Cocoylglutamic acid | 15 |
| N-Myristoylglutamic acid | 10 |
| Sodium hydroxide | 4.7 |
| Potassium hydroxide | 8.3 |
| D-Sorbitol | 20 |
| Butylene glycol | 10 |
| Glucose | 3 |
| Purified water | balance |

(d) A sample of transparent solid detergent of the composition shown in the following Table 7 was prepared and evaluated by the procedures described above. The results were satisfactory in all test items (Example 12).

TABLE 7

| Ingredients | Content (%) |
|---|---|
| Dipotassium N-cocoylglutamate | 40 |
| Monosodium N-stearoylglutamate | 10 |
| Glycerin | 10 |
| Sodium laurate | 3 |
| D-Sorbitol | 10 |
| Myristic acid | 1 |
| Colorant | q.s. |
| Purified water | balance |

Industrial Applicability

The transparent solid detergents according to this invention moisturize with less irritation to skin, hair, ocular mucosa, etc. They have good temperature stability during storage, so that they hardly become colored or emit an odor, or surface active agents hardly crystallize during storage. In general, the detergents according to this invention have good storage stability and good usabilities such as sudsing, disintegration, adhesion, etc., and are especially suitable as facial soap.

We claim:

1. A transparent solid detergent, consisting essentially of N-acylglutamic acid salts, transparentizers, and additives selected from the group consisting of oils, perfumes, colorants, and preservatives, characterized in that said salts are potassium and sodium salts, each having a neutralization degree of between 1.5 and 2.0, said potassium and sodium salts being in a molar ratio of 9:1 to 2:8 and being incorporated in a combined amount of 30 to 70% by weight of the total weight of said detergent.

2. The transparent solid detergent of claim 1, wherein the degree of neutralization is between 1.7 and 1.9.

3. The transparent solid detergent of claim 1, wherein said potassium and sodium salts are in a molar ratio of 8:2 to 3:7.

4. The transparent solid detergent of claim 1, wherein said N-acylglutamic salts are incorporated in a combined amount of 40 to 65% by weight of the total weight of said detergent.

* * * * *